United States Patent [19]
Carey

[11] Patent Number: 5,840,072
[45] Date of Patent: Nov. 24, 1998

[54] ADHESIVE TAPE APPLICATION TO HUMAN SKIN

[76] Inventor: Martin R. Carey, 924 N. 82nd Ter., Apt. B, Kansas City, Kans. 66112

[21] Appl. No.: 69,722

[22] Filed: Jun. 1, 1993

[51] Int. Cl.[6] .................................................. A61M 35/00
[52] U.S. Cl. .............................................. 604/290; 602/52
[58] Field of Search ................... 602/41, 52, 56; 604/289, 290

[56] References Cited

U.S. PATENT DOCUMENTS 4,990,339  2/1991  Scholl et al. ............................ 424/443

*Primary Examiner*—John G. Weiss
*Assistant Examiner*—Mark O. Polutta

[57] ABSTRACT

Apparatus and process for treating ivy or poisonous plant infection or contamination; use of one or more strips of adhesive backed material to draw off the poisonous or reactive liquids from plants and the reacted skin, flesh and the like, caused by the plant contact or exposure, cleaning the infected area.

14 Claims, 2 Drawing Sheets

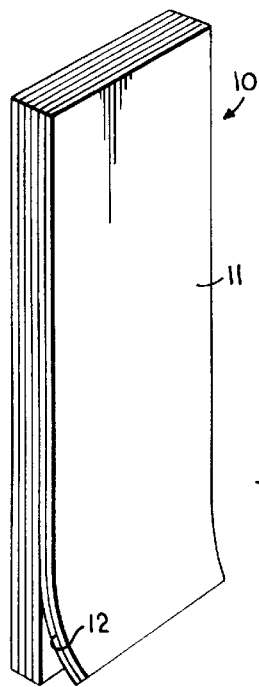
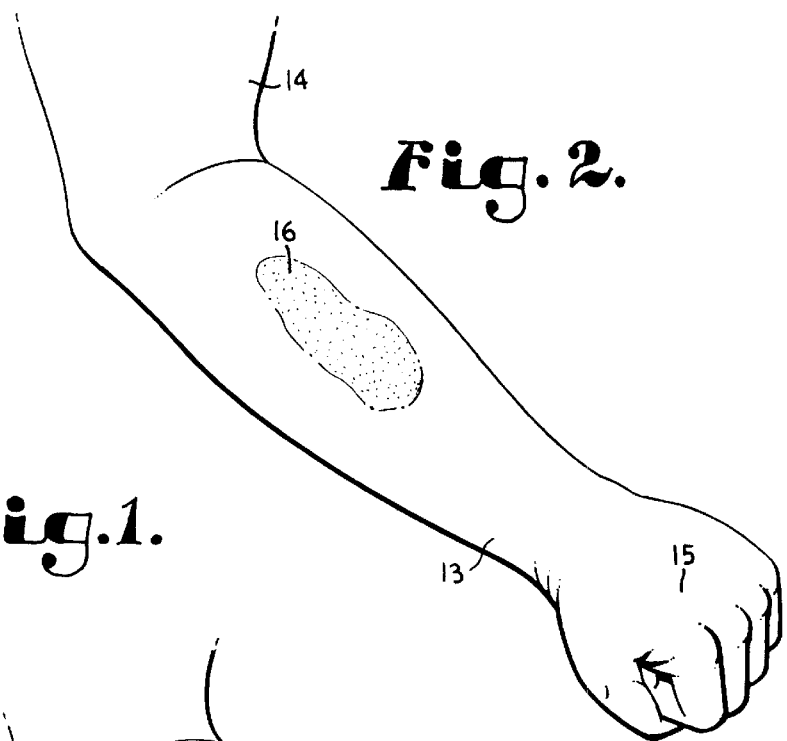
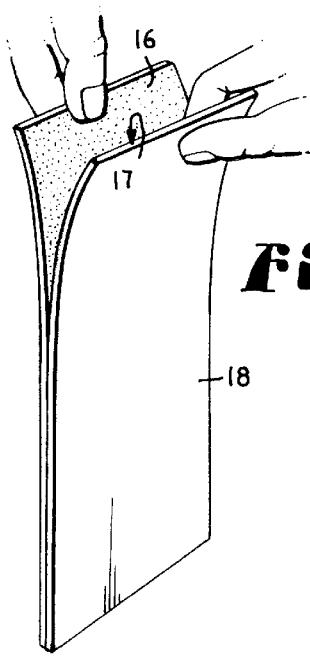
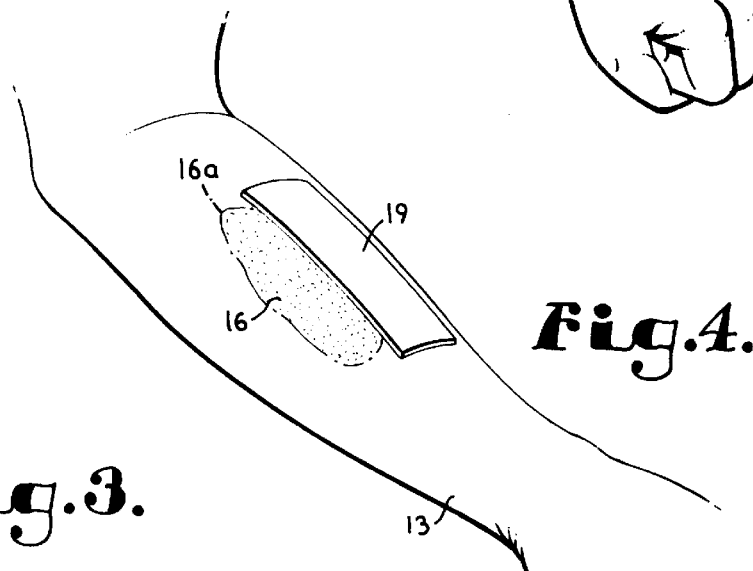
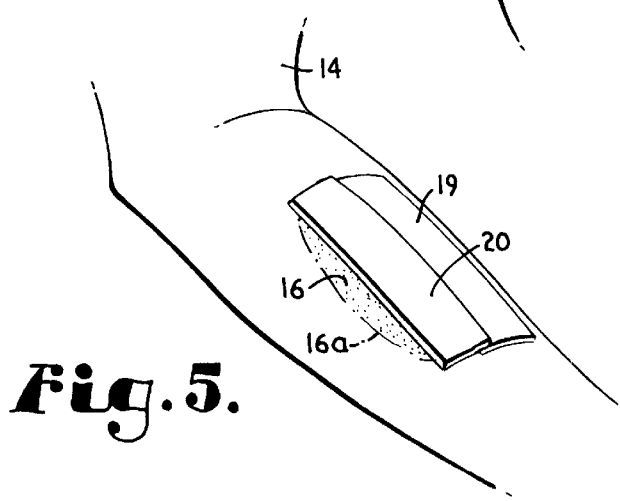

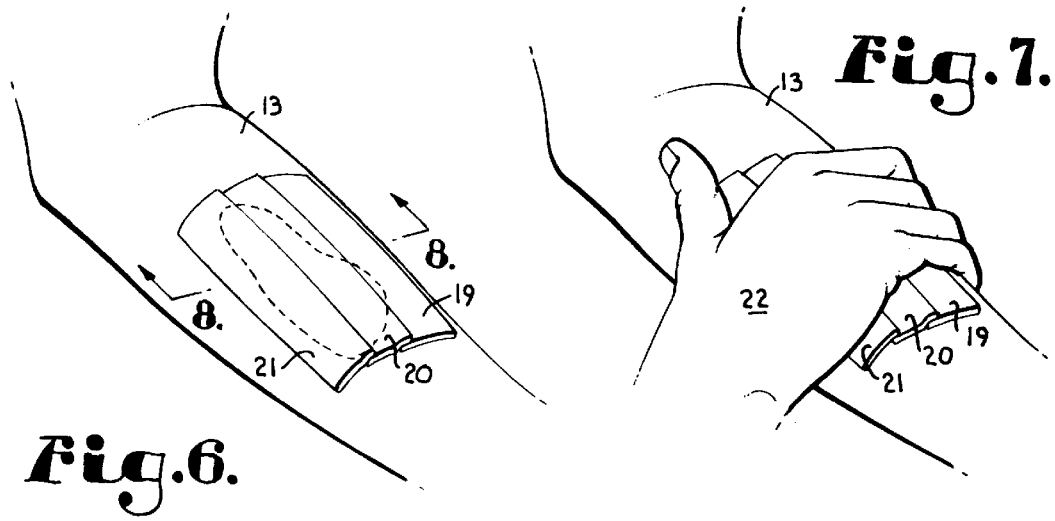
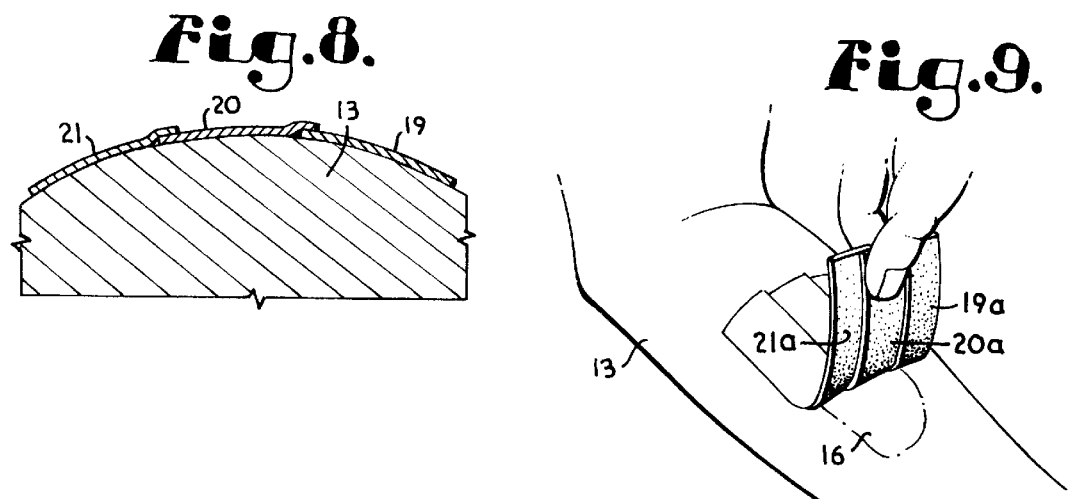
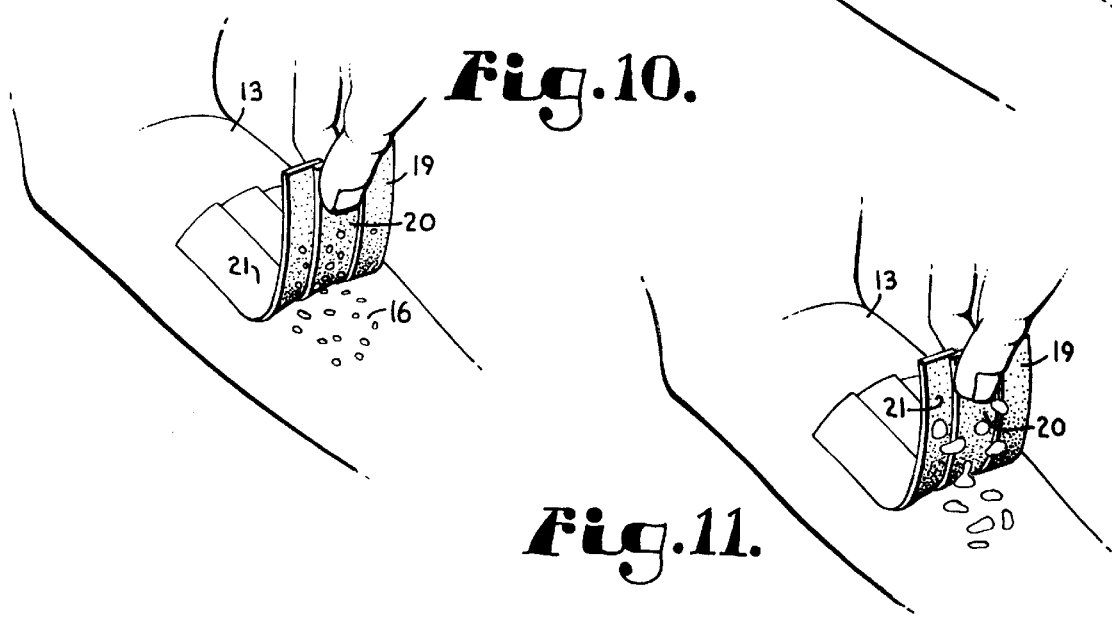

ADHESIVE TAPE APPLICATION TO HUMAN SKIN

BACKGROUND OF THE INVENTION

This development relates to the use of pressure-sensitive tape to help alleviate the effects of poison oak, ivy and sumac contact and contamination on human skin. The improvement is believed to involve the use of the adhesive properties of such tape to assist in removal of poison ivy oils, per se, as well as human skin oils and liquids contaminated by poison ivy oils from the exposed skin, thus to reduce both the potential and/or any actual irritation caused by such poison ivy oils and the skin reaction thereto.

Current remedies for the treatment of the adverse effects of poison ivy, etc. and the contact of poison ivy oils with human skin consists of, typically, creams, ointments or suspensions of various chemicals and substances which are applied to the effected area. Such available treatments are not exceptionally effective in removing poison ivy oils, and loose, dead, oil containing skin and contaminated body surface fluids from the contaminated area. When the treatment application of fluid, cream, ointment or the like dries and flakes off the skin, such ivy oils, etc. may be partially removed therewith. However, such required drying process precludes any rapid removal of such ivy oils from skin contact, thus limiting the effectiveness of such treatments. Further, the actual application of these substances to the affected area combined with the normal human tendency to scratch or rub the affected area (both before and after treatment) tends to spread the ivy oils, etc. and increase the affected skin areas.

BRIEF DESCRIPTION OF THE INVENTION

In order to provide relief from the irritation effects of poison ivy contact with the human skin, the affected area should be covered, as quickly as possible, after exposure, by the application of one or more pieces of pressure sensitive tape with the adhesive layer contacting and engaging the skin. For the most effective treatment, the tape should cover not only the directly affected area but also the area immediately surrounding the affected area. The earlier after exposure the tape application is made, the swiftest results and effects.

Immediate application after contact may even stop rash from occuring as opposed to washing with soap and further spreading water. Gentle rubbing or scratching of the skin through the tape after application may aid in the subsequent removal of poison ivy oils (and oil contaminated skin fluids and contaminated skin) from the affected area with the removal of the tape. Further, perspiration generated under the tape will tend to aid in the transfer of poison ivy oils from the skin to the tape adhesive and in the subsequent removal of the oils with the tape from the affected skin. The tape should be removed from the affected area and the surrounding area when noticeable perspiration or liquefaction has appeared or collected under the tape.

The time frame involved between application and removal of the tape will depend on the physical activity of the individual involved, the sensititivy or reactivity of the individual and on the temperature and humidity of the surroundings. When the tape is removed, in order to prevent contamination of other parts of the patient's body or other people's skin, the used tape can be conveniently folded with the adhesive layer inside and thereafter disposed of safely.

If necessary, to provide further relief, fresh tape may be reapplied immediately to the affected area after removal of the first application of tape, preferably with no attempt therebetween to clean the area, for example, by washing with soap and water. Any such washing will only tend to spread the poison ivy oils still resident on the affected skin to previously unaffected areas.

This discovery and development comprises, with respect to a poison ivy affected individual, the application of pressure sensitive tape to the particular area of the skin which has been affected by contact with poison ivy. Apparently, such application absorbs the poison ivy oils from the skin into the chemicals of the adhesive and/or tackifier. Upon removal of the once applied tape, the objectionable ivy oils are partially, substantially or entirely removed from the affected skin area and can be safely disposed of with the tape. Successive applications of tape, in the case of resistive cases, can be employed.

Thus, a novel approach to relief from the irritation caused by poison ivy sensivitation and poisoning by means of and by virtue of effectively removing those irritant oils from the human skin by the use of tape. Over relatively short times, one or successive applications and removal of original and further pieces of tape (as a sheet) results in more rapid recovery from the highly irritating discomfort experienced by most people from contact with poison ivy with their skin.

SPECIFIC EXPERIENCE

A brief description of the subject applicant's personal experiences leading to the discovery which is the substance of this application is set forth herebelow.

On the afternoon of Jun. 30, 1983, the applicant accidentally and unknowingly made physical contact with poison ivy while working in an area heavily infested with the aforementioned plant. Later that evening, the typical, rash-like symptoms of poison ivy action, reaction or contact appeared.

This was not the applicant's first contact with poison ivy poisoning. That is, applicant had been allergic to poison ivy all his life. Previously, in attempts to allay symptoms as they appeared, applicant had tried such commercially or prescription available remedies as potassium permangante, calamine lotion, IvyDry, Iva Rest and other ointments containing anesthetics such as benzocaine and hydrocortisone. It was applicant's experience that these various remedies, if they had any effect at all, only relieved the itching symptoms for a short period of time and apparently did not remove what the applicant was beginning to realize was the cause of the problem, specifically, the poison ivy plant oils transferred to the human skin by contact with the plant.

Earlier, one bout of poison ivy reaction by applicant was so intense that he had to remain in an air conditioned environment for two weeks because any perspiration caused the allergic reaction to spread.

On the day following the noted Jun. 30, 1983 contact of applicant with poison ivy, applicant went to work in his office. His left arm, the area of contact with the poison ivy, was very uncomfortable. He had the usual very strong urge to scratch the affected area but knew this would simply spread the rash. At this point he began to think of ways to be able to scratch the itching area without spreading the contamination or irritation. Applicant first took a 4×8 piece of paper and wrapped it around his left arm, skin tight and covering the rash. He then placed his arm on the desk top and scratched the paper directly above the rash. Unfortunately, the paper moved slightly due to the scratching motion and caused some spreading of the infection or infestation.

Applicant realized that, if a covering could be found which would stick to the affected skin and not move, he would be able to scratch the itching area with a minimum risk of spreading the rash. Adhesive shipping tape was available in his office. Applicant hypothesized that this tape would adhere to the skin, stay in place and still allow scratching of the rash through the plastic backing.

He then applied a nine inch length of tape to the rash. The tape completely covered the affected area and applicant was able to scratch the tape to relieve the itch (or scratch the itch through the tape). Surprisingly, after a few moments, the itching and the urge to scratch stopped. The tape was left in place so that the rash could be scratched through the tape again when the itch returned.

After about 15 minutes and some more itching and concomitant scratching, the tape started to loosen on the applicant's arm. At this point, he removed the tape and noticed what appeared to be a mixture of perspiration and oils (skin and/or ivy?) adhered to the tape. Apparently, perspiration, which is normally regarded as spreading or able to spread a poison ivy infection or rash was induced by the application of the tape (even in an air conditioned office) yet was effectively trapped by and under the tape. Yet further, contaminated skin and/or poison ivy oils, per se either resident on the surface of the rash or within portions of the rash bearing skin, were also drawn, perhaps by the physics and/or perspiration, perhaps by the scratching and perhaps by the chemistry of the tape out on the surface of the skin, mixing with the perspiration. Both the perspiration and these oils were affectively removed from the skin when the tape was removed.

Applicant then proceeded to repeat the application of tape to the affected area on the rationale that, if perspiration normally would cause a poison ivy irritation to spread, such perspiration, as well as any present natural oils of the skin, most probably contained or carried the active injurious oils of poison ivy. If this were the case, then thorough and/or repeated removal of such contaminated perspiration and skin oils (as well as ivy oils, per se) might eventually (or even swiftly) cause the symptoms of poison ivy contact to be completely relieved.

On this rationale, applicant reapplied tape to the affected area each time there was an urge on his part to scratch the rash or affected area. This lasted for a period of time up to about 12 hours after the first tape application described.

The next day there was no sign of the rash or irritation and, further, no lingering urge or desire to scratch the area. All the symptoms of poison ivy contact had disappeared and the affected area was completely cured.

Over the next few years, the applicant has had several instances involving inadvertent and unsought contact with poison ivy. By using the successive tape treatments as described above, the allergic irritations have been cured, in every case, overnight. In the case of these more recent instances, it became evident that the sooner the tape was applied after contact with poison ivy, the faster was the ensuing relief and eventual cure and the less the virulence and area of the infection.

THE PRIOR ART

General background on the composition, nature and characteristics of various pressure sensitive adhesive tapes may be found in the follwing:

(1) Pressure Sensitive Adhesives Tapes Mukhopadhya, Gautom et al, Department of Plastics Technology, HB Technological Institute, Kanpur, India (Paintindia, December, 1973 page 23).

(2) Taking A Look At Tape And Film Adhesives, Harry King, Adhesives Age, February, 1972, page 22.

(3) Pressure Sensitive Tapes, Clauser, H. R., Materials And Methods, Manual No. 125, March, 1956.

(4) Pressure Sensitive Adhesives And Their Applications Hodgson, N. E. from Adhesion (London) Volume 3, pages 207–20, 1979.

Applicant is aware of the following patents of questionable relationship to the subject method.

Zaffaroni, A. U.S. Pat. No. 3,734,097, issued May 22, 1973 for "Therapeutic Adhesive Tape".

Cardarelli, N. F. et al, U.S. Pat. No. 3,749,772, issued Jul. 31, 1973 "Dermal Protective Film".

Moore, W. T., et al, U.S. Pat. No. 4,497,823, issued Feb. 5, 1985 for "Therapeutic Method To Reduce Pain And Inflammation".

Robinson, J. R., U.S. Pat. No. 4,615,697, issued Oct. 7, 1986 for "Bioadbesive Compositions And Methods Of Treatment Therewith".

Bolton, L. L. et al, U.S. Pat. No. 4,668,228, issued May 26, 1987 for "Debriding Tape".

OBJECTS OF THE INVENTION

A first object of the invention is to disclose and detail the use and effects of pressure sensitive tape in slowing, preventing and alleviating the effects of poison ivy (poison sumac) contact, contamination and reaction on the human skin.

Another object of the invention is to provide a unique use of a unique material (pressure sensitive tape) and a unique process of using such whereby to assist in removal of poison ivy (sumac) oils, per se, human sweat, poison ivy oil contaminated human sweat, skin fluids produced by reaction to poison ivy skin contact, human skin oils and liquids contaminated by poison ivy oils from the exposed and/or ivy poisoning reacting human skin.

Another object of the invention is to be able to more swiftly reduce skin irritations, rashes, swellings and the like caused by poison ivy (poison sumac) oil skin contact as soon as certain means (pressure sensitive tape) are available or at hand to the ivy-infected, exposed or contaminated person.

Another object of the invention is to provide new means and methods for treating poison ivy, poison oak and poison sumac exposures, infections and contaminations, wherein physical (as opposed to applied medicines) means are employed to obtain the desired and necessary effects.

Still another object of the invention is to provide poison sumac (ivy, oak, sumac, etc.) treatments, methods of treatment and means for treatment all of which take into effect the fact that the human skin is normally covered by a substantially continuous layer of dead skin flakes, pieces and particles, which layer's fragments offer effective berths and receiving zones for poison sumac, etc. oils, such being at least one of the factors that makes the exposure to such oils so difficult to treat and clear.

Another object of the invention is to provide means for treating poison (sumac) ivy contact, infestations and infections wherein the treatment may be applied at any stage of exposure, specifically (1) immediately upon exposure if the exposure is known or detected and the treatment means are at hand; (2) immediately upon first reaction of the human skin to the noxious oils and plant liquids and (3) any time thereafter, including after the typical blisters and lesions of poison sumac, ivy and oak have formed. (4) Long lasting cases may also be treated successfully.

Yet another object of the invention is to provide unique treatment methods for effectively limiting and containing the zone and area of the contact followed immediately by treatment; thus confinement, covering and limitation of action and area of the contact is then followed by removal of dead skin fragments, the poison ivy oils per se, human sweat, mingled fluids including the ivy contaminant, etc.

Yet another object of the invention is to provide such a method and means of treating and controlling poison ivy and poison sumac exposure wherein hunters, campers, firefighters, armed forces training in wild areas, logging personnel and the like may carry with them the means for immediate treatment and control of a poison sumac/ivy/oak exposure.

Even yet further an object is to provide a method of treatment of poison sumac/ivy/oak exposure preferably before any cleaning or washing of the exposed body area is undertaken.

Yet another object of the invention is to provide a means of immediately treating poison sumac, etc. exposures in such manner as to greatly reduce the quantity of poisonous elements of the plant oils that actually get into the contacted individual's system, whereby to minimize sensitization of the individual by the poison sumac, ivy or oak.

Other and further objects of the invention will appear in the course of the following description thereof.

BRIEF DESCRIPTION OF THE DRAWINGS

FIG. 1 is a three-quarter perspective view from above of a stack of one-sided adhesive strips of sorts which are commercially available in various sizes.

FIG. 2 is a view of the forearm of the left arm of a potential user (with an initial infection shown) of the subject invention.

FIG. 3 is a view showing plastic and adhesive sheeted strips of FIG. 1 being separated from one another for use in the process to be described hereinafter.

FIG. 4 shows a first sheet analogous to those of FIGS. 1 and 3 placed over part of the infection zone and including the edge of the contaminated area.

FIG. 5 is a next stage in the process of FIG. 4 where a second strip is placed one edge over the first sheet (preferably) and the balance thereof over part of the contaminated area and longitudinally therebeyond.

FIG. 6 is a showing of the contaminated area of the earlier figures fully covered by (in this case three sheets) a number of sheets of the adhesive faced sheets.

FIG. 7 shows the use of the hand of the actor or tainted individual (right hand) or the right hand of a comrade working the overlapping sheets to give deeper access to the adhesive of the sheets and chemicals and skin to the contaminated area.

FIG. 8 is a view taken along the lines 8—8 of FIG. 6 in the direction of the arrows.

FIG. 9 is a ¾ perspective view from above of the hand of the contaminated person or his comrade removing the pad or set of interlocked sheets from the infected area.

FIG. 10 is the same thing as FIG. 9 except for the fact that a much more serious infection or contamination is indicated by the larger spots. This probably will require one or more additional Applications to clean the entire area of any oily plant liquids, skin particles, human liquids, etc.

FIG. 11 is the same thing as FIGS. 9 and 10 except for the fact that a very serious infection is shown because of the size of the lesions and possibly blisters caused by the contamination.

FIG. 1 is a vertical schematic view of one commercial form of plastic sheet(s) or sheaths, for such are initially adhesively attached to one another on one side thereof. Each sheet, starting on either side can be individually separable from one another. There is a non-adhesive sheet 11 in each individual piece and an adhesive sheet attached thereto, making the two elements integral and offering and adhesive sheet and a non-adhesive sheet when the individual member is prepared for use.

FIG. 2 shows the forearm 13 of an individual with upper arm 14 and hand 15. An initial zone of action, reaction or infection is seen at 16 in the view. This could be larger (the entire arm) or smaller.

FIG. 3 shows, for a single sheet of the plastic adhesive sheathing that the adhesive cover or initial adhesive cover may be pulled off, exposing the adhesive side of the sheet. This differs from what is seen in FIG. 1. 16 is the original adhesive sheet, 17 the adhesive sheet to be used and 18 the non-adhesive side.

FIG. 4 shows the arm of FIG. 2 with a first elongate sleeve or sheath of adhesive-based and non-adhesive top material 19 being applied to one edge of the exposure area 16. The edge 16a is covered the length of the sheet or nearso, but an entire portion of the sheath is off the exposure zone 16.

FIG. 5 is a view like that of FIG. 4, more fragmentary with respect to the arm showing a second sheet adhesive portion applied to the inner edge of the first sheet and overlying the exposure zone. The edge toward the viewer, 16a, is not yet covered, but a relatively large portion of the exposure zone is.

FIG. 6 is the step past FIG. 5 where the entire exposure area has been covered by a uniform, continuous, self-adhesive sheet of individual strips. The same result, of course, can be achieved by ripping of successive lengths of adhesive tape having effective adhesive from a roll thereof and applying such in the order seen in the FIGS. 2–6, inclusive. The sheath or sheet which overlie both a portion of the body of the exposure area and its leftmost edge is numbered 21. Note the full length overlap of one edge of pieces or sheets 21, 20 and 19, in that order. This is best seen in FIG. 8.

In FIG. 7 is shown the hand 22 of the user, operator, doctor or exposed person him/herself working or handling the bandage unit or sheet that the adhesive is fully put into contact with the exposed zone and any plant secretion, human secretion, skin bits and the like.

As noted, FIG. 8 is an end view (from the right hand sides of FIGS. 6 and 7) of the assemblage of adhesive applying sheets showing how the sheets overlie the skin and, at one edge of each, the adjacent sheet.

FIG. 9 shows how the integral layer of individual sheets, adhesive to one another at the edges and see in FIG. 8, after working thereof, as in FIG. 7, preferably, and staying in body contact for a number of minutes is removed from the zone of exposure or infection 16, carrying therewith plant and human liquids and skin particles loosened by the action of the toxin.

FIG. 10 is a view like FIG. 9, except for the fact that a later stage is involved in that it can be seen that vesicles, nodules, blisters and the like have developed so that the first removal of sheeting and materials (liquids and skin particles) will be patterned according to the skin lesion pattern. This situation calls for much larger effort in overcoming (curing) same than the lightest first contact seen in the earlier views, probably. Second, third and fourth applications of new sets of sheets with intimate contacting of the adhesive layer where the fluids and materials of the skin thereunder typically takes place. Each layer is typically worked as in FIG. 7.

FIG. 11 is a stage in the exposure or infection of the skin, here of the forearm, involves highly serious lesions having appeared in the situation with considerable fluid in the zone and considerable skin surface involvement, open and closed, both. Numerous applications of sets of sheets as seen in FIGS. 6–10 will be applied to clear the area of noxious fluids, reaction excretion from the skin and pieces of skin and flesh which may be loosened by the action in question.

FURTHER INFORMATION

Phase 1 of a poison ivy infection may be used to refer to a light exposure to poison ivy/poison sumac wherein a rash has not yet formed yet the subject is aware of the contact and of the area affected. In this situation, if tape strip application is immediately undertaken, two applications should be substantially 100% effective. In this case the first application should be carried out for approximately three minutes, immediately followed by an additional application of some three more minutes.

For the purposes of this application, a Phase 2 exposure refers to a situation where an initial rash has appeared or is in the process of appearing. In this situation, three prompt applications of tape as previously described should render satisfactory results. The first application should be of approximately three minutes, followed by an application of another three minutes, then followed by a final application of fifteen minutes.

For the purposes of this application, a Phase 3 infestation refers to the existence on the user's skin or patient's skin of the typical poison ivy, oak, sumac rash including, as well, small blisters appearing and general swelling of the contaminated skin area plus, unless treatment begins quickly, spreading of the reaction. Here the affected area should have two applications as described above in Phase 1. Thereafter, it should be treated by a 10 to 15 minute application which will allow perspiration a chance to move the poison ivy oils to the surface of the skin so that it then can be more readily absorbed by the tape materials. Such longer application can be repeated three to four times afterwards to make sure that the poison ivy oils are removed from the lower surfaces and pores of the skin. In the case where blisters have formed, it is important to vigorously scratch these blisters (which are already itchy) with the tape in place. The vigorous scratching of these small blisters operates to break them open and cause fluids to contact and appear on the tape. After the fluids have appeared, it is best to go ahead and move the tape and use another piece of fresh tape for one minute followed by another application of one minute.

It is critically important that, in each application, that new pieces of tape are used and that the old contaminated tape bodies are properly disposed of. It is further important also that if, at any time, an itch persists in a contaminated zone, to cover again, with tape, the itchy area. Any additional areas on the body that itch or begin to itch before or during treatment should be treated the same.

It is most useful to limit physical activity of the exposed person to avoid heavy perspiration over the general body or particular perspiring areas which may spread the poison ivy oils and chemicals.

Any affected, uncured area that comes in contact with a yet not affected area should cause the new area to be additionally be treated as described in Phase 1, for example, wrist to legs or upper inner part of arm to side of chest or inner finger to inner finger, etc.

All times listed for application may vary with ambient temperature, physical activity levels and oil contents on the skin independent of the ivy contamination, such as sun screens, suntan oil, etc.

The relatively short time applications are designed to remove the poison ivy oils on dead skin particles and flakes on the outer or upper part of the skin by the mechanical and chemical properties of the use sides of the tape. Longer applications are employed to allow perspiration and natural human oils to absorb and bring the poison ivy oils and chemicals to the tape, in addition to removing dead skin particles which may be covering over poison ivy oils on the skin below. In the case of the longer time application of the tape, if the tape works itself loose due to the presence of perspiration and oils, it has done its job and should be immediately replaced with a new piece of tape.

The more sensitive parts of the body can also be treated with the tape. However, a tape with more tackifier and less adhesive properties, for example Scotch Magic Tape or equivalent other commerically available tapes having similar tack will permit application to eyelids, genitals and any areas of skin that might have hair. Application to genitals and eyelids should be limited to one minute. Areas with hair that are not too tender or sensitive can be allowed the longer applications and the less sticky tape allows the hair present to be pulled less.

STRUCTURE, FUNCTION AND USE

A very large number of contingencies can arise when Poison Ivy or Poison Sumac contamination or contact is experienced by the human body. This is also the effect with respect to other related chemicals, such as synthetic chemicals and man made chemicals, as well as other natural but antagonistic organic or biological chemicals. The range and level of the contact or contamination can vary from a small touch (such as just a brush on the arm or leg from the plant leaves or a small peripheral spray from an industrial source) to actual total full body contact and anywhere in-between. Clearly there are going to be circumstances which require, as quickly as possible, urgent medical and hospital attention. However, there are circumstances where, whatever the level of contamination or exposure, there is no immediate or even reasonably near professional or even skilled aid or help.

The point here is that, even in the most extreme emergency situations, this avenue and type of adhesive tape application to skin contaminations of an oily, non-water soluable chemical sort, particularly natural contaminations such as poison ivy and sumac, can be helpful, useful, indeed near life (and/or sanity) saving. For a person to be required to walk or hike through, for example, woody or forested areas for many hours or days before treatment or relief by conventional medical sources is available, where there is near whole body, half body, arms and/or legs, facial, etc., exposure to hazardous plants can be most agonizing, uncomfortable, and irritating, even disabling. Where there is a relatively large area exposure, particularly of the arms and hands, it is very difficult to prevent eye and nose/mouth/ear contamination, as well as other most sensitive and irritable parts of the body.

The presence of two or more people in a hunting, hiking or exploring trip will aid in the ability to effect treatment of all contaminated body areas. Hikers and woodsmen often, depending on weather, wear no more than shorts and shoes, leaving large body areas exposed in case of a fall, necessary traverse of a noxious plant infested area, etc. Poison ivy and sumac both climb on tree trunks, fence posts and the like, as well as infesting the ground.

The following stages of treatment are preferably employed:

(1) As soon as contact with a noxious oily chemical agent is noted, or the beginning or maturation of a reaction thereto, the affected area should be defined as well as possible, strips of tape should sequentially be removed and separated from the source or roll thereof, and the tape strips sequentially aligned and applied to as much of the directly affected area as possible, including the zone or area immediately surrounding such actually affected area. Preferably successive tape strips will be overlapped at the edges thereof to make a full continuous contact.

(2) Clearly, chemical, plant or other noxious liquid skin contamination which is water soluble should be treated by water washing, often overhead full body nude spray showers followed by repeated soap and water washings and rinsings. The subject treatment disclosed here is directed to skin contaminations which are not subject to cleansing or relief by water, soap and water, or water and detergent, etc., treatments. In the case of poison ivy and poison sumac, it is well known that washing of the effected area generally merely spreads the plant oils and contaminations to other parts of the body. Taking a bath after a thorough skin contamination by poison ivy may result in near or entire, full body contamination.

(3) After the application of one or more strips of adhesive tape to the selected contaminated zone to be treated initially, first gentle, then harsher rubbing or scratching of the outer surface of the tape, forcing its adhesive side against the skin, well may aid in subsequent removal of contaminating or contaminated materials, including the original contamination source, oil contaminated skin fluids and contaminated skin or skin particles. Preferably, the initial application of tape is maintained in place until at least some perspiration is generated thereunder, whereby to aid in the transfer of contaminated substances from the skin to the tape adhesive.

(4) The tape should be removed from the overlaid area when noticeable perspiration and/or liquefaction of any sort (contaminating liquids, contaminating oils, skin liquids, skin oils, skin fragments carried thereby) have appeared or collected under the tape. It is best to employ at least a translucent, but preferably a transparent or near transparent adhesive tape in this Application so that the effect of the application of the tape to the effected or contaminated zone, as well as the reaction of the skin to the situation, has appeared or does appear.

(5) It is conceivable that some person or persons will be allergic to the application of any particular tape. In this case, if it is determined that the reaction is due to the tape either in place of or in addition to the reaction to the oily contaminant, the tape treatment should not be used. This would be very unusual. It should be suggested that, upon application to or receipt of ivy or other natural or industrial oily substance contaminants to the skin or contamination of the skin thereby, use of any tape not known to be corrosive or caustic to the skin of man should be tried. This can be done on a very limited area at first, to test the action and success of the treatment. It should be kept in mind that once a severe case of ivy poisoning (or other chemical contamination) has occurred, the individual is often highly sensitized to and much more vulnerable to, as a rule, later ivy or such other material contaminations.

(6) The elapsed time a given tape application is useful to the given individual will depend upon the chemical agent itself, physical condition of the individual involved (for example, is the individual sweating from heavy physical activity, etc.), the sensitivity or reactivity of the skin of the individual, the temperature and humidity of the surrounding environment and air, other factors and the like.

(7) When the first laid set of strips (or body of tape strips) is removed from the zone first treated, in order to prevent contamination of other people or other parts of the exposed individual's body, the used tape strips or integrated body are folded upon themselves with the contaminated adhesive layer inside. Such thereafter should be disposed of by burying or discarding into a suitable waste disposal container.

(8) Recalling that the state of the zone or zones to be treated or being treated may range from (1) pre-skin reaction (2) through inflammation (3) through formation of blisters or vesicles to (4) existance of areas of weeping or bleeding blisters and/or vesicles, clearly one tape treatment may not be sufficient. Therefore, if liquid or oil remains on the skin surface in the effected area or the irritation remains (sensation of itching, burning and the like), subsequent or sequential tape applications of the same type should be employed. Preferably no intermediate treatment should be given between successive tape applications, as the entire point of the tape application is to absorb and remove the oils, liquids, contaminants, chemicals, contaminated skin particles and the like from the area. Washing with water or soap and water, etc., very well may only tend to spread some of the contaminant oils perhaps or probably still resident on or in the affected zone.

(9) In multiple area contaminations or large area contaminations, the contaminated person and/or his companion(s) must select whether to fully treat a limited zone, particularly a very sensitive or functionally important zone repeatedly before the rest of the areas or zones also contaminated. Generally speaking, and depending on the overall conditions, immediate, swift treatment of all contaminated areas should preferably take place. The object is to get the corrosive or contaminating oily substances out of contact with the skin as soon as possible and preferably before a massive physiological or biochemical reaction by the body or skin takes place.

The term "pressure-sensitive tape" as used herein denotes commercially available tapes consisting of a backing material or plastic film (transparent or translucent, such optimum), metal foil, textile or paper and an adhesive. This adhesive typically consists of an elastomer and a tackifier as well as other minor ingredients. The elastomer may consist of rubbers or synthetic viscoelastic polymers, especially poly(alkyl vinyl) ethers, poly(alkylacrylate) esters, including but not limited to polymers, copolymers or block polymers of one or more of the following:—styrene, butadiene, acrylonitrile, isoprene, isobutylene, alkylstyrenes, ethylene, vinyl acetate, chloroprene, alkylacrylates, acrylic acid, trimethylamine, methacrylamide, acrylamide, vinylpyrrolidone and vinylbutyral.

The tackifier typically consists of or may consist of thermoplastic or thermosetting resins including, but not limited to, rosin and rosin derivatives, coumarone-indene resins, oil-soluble phenolics, low molecular-weight polystyrene, polyterpenes and petroleum hydrocarbon resins.

Aside from the irritation, blistering, vesicling, the blister and vesicle rupturing, spreading of the contaminant chemicals and oils, particularly by the blister and vesicle rupturing, liquid smearing or transfer, and perspiration, as well as the sometimes ultimate scarring of the skin of the contaminated person, there exists the often unbearable itching and burning of the reaction and the victim's desire to scratch the contaminated area. It is perhaps difficult for those who have never suffered a substantial ivy poisoning or contamination to realize the intensity of this irritation and the urge to rub, scratch or even claw at the affected zone.

One of the very important effects of the use of the subject method and procedure is to enable the individual who has been contacted or affected to rub or scratch the affected area once the tape has been applied. This, of course, must be done with some discretion in that the tape should not be ripped off or displaced. However, rubbing, scratching and contact not only will relieve some of the itching and burning, but affect the more complete contacting and mixing of the adhesive elements of the tape with the skin contaminants. The tape adhesive or successive applications of tape adhesive must absorb, adsorb, mix with, pick up or adhere to the contaminating oils, the skin liquids including perspiration, the skin liquids which have been contaminated by the intruding agent, particles of loose skin which have been soaked, covered or contaminated with any of these liquids, etc. At least a limited amount of rubbing, massaging and/or scratching aids this process.

An index of the effectiveness of the treatment is when the irritations, itchings, skin reactions and the like lessen and disappear. This set of measures helps determine the number of tape applications to be applied. A single application may last from two to ten minutes, as a not limiting but typical example, particularly depending upon the amount of contamination received and skin reaction therefrom that has already taken place, the presence of a considerable amount of liquid usually lessening the time of a given tape application.

In the case of a suspected contact area which has not yet started to substantially react or itch, tape may be applied thereto, massaged, rubbed or scratched and left in place for a limited time to pick up whatever contaminating oils may be present. It is also not necessarily a negative effect to have blisters or vesicles (if formed) break to release inner skin liquids in this tape treatment. The object of the tape treatment is to remove from the contaminated areas all liquids which may contain or continue the contamination and/or skin reaction or spread it. It is well known that blister and vesicle bursting or weeping of poison ivy contaminated areas (uncontained) will generally carry the infestation and contamination to larger and surrounding skin areas. Accordingly, it may be assumed that the contaminating oils themselves have or may have penetrated a certain portion of the skin and mixed with natural skin oils and liquids at any stage or reaction.

In this use of tape, there rarely is any residue which is left to discolor clothing. Additionally, there rarely remains any discoloration of the skin as is the case in many medical treatments or chemical applications know to the art.

In the event there is not enough tape to effect the optimum treatment of all contaminated areas, the individual contaminated must be or is necessarily transported, one way or another, even if by only his own feet, to a place where medical treatment and/or more of the tape applications may be obtained for all body zones. Any untreated areas are naturally going to tend to contaminate the rest of the body, but those portions cleared may stay cleared for some time. This is the case, particularly where no water washing is employed.

From the foregoing, it will be seen that this invention is one well adapted to attain all of the ends and objects herein above set forth together with other advantages which are obvious and which are inherent to the materials and procedures.

It will be understood that certain features, steps, sub steps and sub combinations are of utility and may be employed without reference to other features, steps and sub steps and combinations. This is contemplated by and is within the scope of the claims.

As many possible embodiments may be made of the invention without departing from the scope thereof, it is to be understood that all matter herein set forth is to be interpreted as illustrative and not in a limiting sense.

I claim:

1. A process of treating human body exposure to noxious chemicals including such from plants such as poison ivy and poison sumac including the steps of:

(1) as soon as contact with a noxious, oily, chemical agent is noted, including the beginning or maturation of a reaction thereto, first defining as well as possible the limits of the affected or exposed area(s);

(2) providing strips of adhesive tape of a sufficient length to extend at least the length of the defined affected area and sequentially applying said strips longitudinally parallel or substantially parallel to one another with at least some overlap thereof whereby to, as swiftly as possible, cover the entire defined affected area adhesive side in;

(3) after the application of at least one, more or many strips of adhesive tape to cover the defined contaminated zone to be treated, first, gently, then more harshly, rubbing and scratching the outer surface of the entire tape, whereby to force essentially its entire adhesive side against the entire defined affected skin area;

(4) maintaining the initial cover, blanket or body of tape in place on the said defined affected area until at least some perspiration or visible body fluid, plant oils or combinations thereof are generated thereunder, thus to aid in the transfer of contaminated substances from the skin to the adhesive of the tape;

(5) when noticeable perspiration and/or liquifaction of any sort (contaminating liquids, contaminating oils, skin liquids, skin oils, skin fragments carried thereby, combinations thereof etc.) have appeared or collected under the tape, removing the body of the tape application from the overlaid area in such manner as to not contact any other part of the exposed individual's skin with the working (adhesive) side of the tape;

(6) examining the state of the defined exposure zone of skin to determine the status of the infestation from (a) pre-skin reaction, (2) through inflammation, (3) through formation of blisters or vesicles to (4) presence of areas of weeping or bleeding blisters and/or vesicles;

(7) if such are present, then repeat the tape application in single or multiple sequences until the skin surface liquids are substantially cleared from the area.

2. A process as in claim 1 wherein successive strips of tape are removed from a source thereof.

3. A process as in claim 1 wherein the defined affected area is itself completely covered by the body of adhesive tape and, as well, circumferentially, the zone or area immediately surrounding such actually affected area.

4. A process as in claim 1 wherein chemical, plant or other noxious liquid skin contamination which is at least partly water soluble is first treated by water washing, such as overhead full nude body spray showers, followed by whole or part body repeated soap and water washings and rinsings.

5. A process as in claim 4 wherein the chemical, plant or other noxious liquid skin contamination is not entirely water soluble and, after the said water washing and rinsing, the subject tape contact and transfer treatment is applied to each of those skin area contaminations not effectively subject to cleansing or relief by water, soap and water, water and detergent, etc. treatments.

6. A process as in claim 1 wherein any water soluble skin contamination is of less threat and the nonwater soluble contamination, if washed, tends to spread the irritant oils and contamination to the other parts of the body, the process of using the tape treatment with respect to the most serious nonwater soluble contaminated zones of the body before any water washing of the body.

7. A process as in claim 1 wherein, after the application of one or more strips of adhesive tape to the selected contaminated zone to be treated initially and particularly after entire tape sheet coverage of the contaminated zone, utilizing, first, gentle, then, thereafter, harsher rubbing or scratching of the outer surface of the tape, whereby to force its inward adhesive side against the affected skin, whereby to aid in subsequent removal of contaminating or contaminated materials, including the original contamination source, oil contaminated skin fluids, contaminated skin and skin particles and combinations thereof.

8. A process as in claim 1 wherein the first laid set of adhesive tape strips (or entire body of first laid tape strips) is integrally removed from the body zone first treated, and, in order to prevent contamination of other people or other parts of the exposed individual's body, the used tape strips or integrated body of used tape strips are folded in upon themselves with the working (adhesive) layers or surfaces in contact with one another, i.e. with the contaminated adhesive layer inside, whereby same can be handily be buried or discarded into a suitable waste disposal container.

9. A process as in claim 1 wherein multiple body area contaminations by at least one noxious chemical substance have taken place, including large area such contaminations, including the step of selecting whether to fully treat a limited body zone, particularly very sensitive or functionally important such zones, repeatedly, before the rest of the body areas or zones also contaminated are treated.

10. A process as in claim 1 wherein immediate, swift treatment of all or as many contaminated areas possible to be nearly simultaneously treated preferably takes place, whereby to get all or as much as possible of the skin corrosive or contaminating oily substances out of contact with the skin as soon as possible and certainly preferably before a massive physiological or biochemical reaction by the individual's physiological systems, body or skin has taken place.

11. In a body contamination of the skin by industrial, organic or natural chemicals resulting in irritation, blistering, vesicling, blister and vesicle rupturing, spreading of the contaminate chemicals and oils, particularly by blister and vesicle rupturing, liquid smearing or transfer and perspiration, as well as the sometimes ultimate scarring of the skin of the contaminated person, all of such being most serious happenings and reactions, there further exists thereamong the personally felt, often unbearable itching and burning of the reaction with the victim's desire to scratch the contaminated area overwhelmingly present, here applying successive strips of tape to cover one or more of said contaminated body areas in such manner as to form a body of overlapping strips which is both wide enough to and long enough to fully cover the area, then causing the individual being treated to rub or scratch the affected area, once the tape has been applied, in such manner that, while the tape is not ripped off or displaced, the rubbing, scratching and contact will not only relieve some of the itching and burning by removing chemicals from contact with the skin area, but also affect the more complete contacting and mixing of the adhesive elements of the tape with the skin contaminants, the tape adhesive or successive applications of tape adhesive covers or bodies absorbing, adsorbing, mixing with, picking up or adhering to the contaminating oils, skin liquids including perspiration, skin liquids which have been contaminated by the intruding agent, particles of loose skin which have been soaked, covered or contaminated with any of the liquids, etc.

whereby at least a limited amount of rubbing, massaging and/or scratching not only aids the process in successive tape applications and removals but gives sensational relief to the patient.

12. A process of treating a first phase (Phase 1) of a noxious chemical reagent involving a relatively light exposure to an only substance such a poison ivy/poison sumac, wherein a rash has not yet formed, yet the subject is aware of the contact and of the area affected, the process which comprises first applying one or more adhesive tape strips over the area infected so as to cover at least substantially the entire length and width thereof, the tape strips sequentially axially aligned and edge overlapping one another at the edges thereof and applied to as much of the directly affected area as possible, including at least some of the zone or area immediately surrounding the actually effected area, the tape strips at least slightly edge overlapping whereby to furnish a complete, continuous tape body or sheet overlying the affected area, carrying out the said first application for approximately 3 minutes, removing said first sheet, following the latter by an additional, second application of a sheet of overlying, contacting adhesive tape for approximately 3 more minutes.

13. A process of treating a second phase (Phase 2) exposure of at least a portion of the human body to a noxious chemical reagent such as a poison ivy/poison sumac contamination, wherein an initial rash has appeared or is in the process of appearing, whereby the subject is both fully aware of the contact and of the area initially affected;

applying a first adhesive tape sheet application to the affected zone, the length of portions of the tape sheet extending past the length extremities of the zone and the width of portions of the tape extending past the width extremities of the zone, any tape strips employed, adjacent to one another, overlapping so as to give a unitary sheet thereof, there being at least three successive zone covering and contacting applications of tape sheets, the first application being of approximately three minutes, the second application being of approximately three minutes and there then being a third application of substantially 15 minutes.

14. A process of treating a third phase (Phase 3) infestation or contacting of the human body skin by a noxious chemical substance such as poison ivy, poison oak and poison sumac where already the human skin reaction rash exists on the patient's skin typically including, as well, small blisters present or appearing, as well as present or occurring general swelling of the contaminated skin area wherein, unless effective treatment begins quickly, wide spreading of the reaction area will occur, comprising the steps of making two applications, sequentially, of adhesive tape sheets over the affected areas, the width of the strips making up the sheets being greater, in combination than the width of the affected area, the length of the said strips being of greater length than the affected area, the adjacent longitudinal edges of said tape strips overlying one another to produce an integral, affected area overlying, blanket or sheet of adhesive tape, including sequentially making two applications of such tape sheets over said Phase 3 infected area, the applications running approximately 3 minutes apiece, then sequentially applying a plurality of 10 to 15 minute tape sheet applications to the affected area, whereby to allow human perspiration and skin fluids a chance to move the poison ivy oils to the surface of the skin for more ready absorption by the adhesive face of said tape material, the number of repetitions of said longer time applications depending on when all the visible skin liquids, including perspiration and poison ivy oils, are removed from the lower surfaces and pores of the skin zone affected.

* * * * *